United States Patent
Mercer

(10) Patent No.: US 6,274,850 B1
(45) Date of Patent: Aug. 14, 2001

(54) APPARATUS AND METHOD FOR IDENTIFYING SUBJECT MEDIUM WITHIN COOKING DEVICE

(75) Inventor: Gary L. Mercer, Eaton, OH (US)

(73) Assignee: Henny Penny Corporation, Eaton, OH (US)

( * ) Notice: Subject to any disclaimer, the term of this patent is extended or adjusted under 35 U.S.C. 154(b) by 0 days.

(21) Appl. No.: 09/361,234

(22) Filed: Jul. 27, 1999

(51) Int. Cl.[7] .............................. H05B 1/02; A47J 37/12
(52) U.S. Cl. ..................... 219/492; 219/441; 99/325; 99/332; 99/342; 99/403; 99/DIG. 11
(58) Field of Search ...................... 219/492, 490, 219/509, 441, 442, 435, 425, 704, 412; 99/342, 343, 344, 325–326, 327, 331–332, 403, DIG. 11; 392/312, 323, 316, 334, 441, 447

(56) References Cited

U.S. PATENT DOCUMENTS

| | | | |
|---|---|---|---|
| 1,923,889 | * 8/1933 | Sauter | 99/325 |
| 2,655,859 | * 10/1953 | Bell | 99/325 |
| 3,385,955 | * 5/1968 | Tucker | 99/325 |
| 3,842,724 | * 10/1974 | Korr et al. | 99/358 |
| 4,058,703 | 11/1977 | Price . | |
| 4,131,773 | 12/1978 | Maham et al. . | |
| 4,197,581 | 4/1980 | Watrous et al. . | |
| 4,251,809 | 2/1981 | Cheney . | |
| 4,282,423 | 8/1981 | Volz . | |
| 4,296,310 | 10/1981 | Luebke et al. . | |
| 4,372,980 | 2/1983 | Luebke et al. . | |
| 5,051,921 | 9/1991 | Paglione . | |
| 5,067,345 | 11/1991 | Mougne . | |
| 5,086,324 | 2/1992 | Nemeth . | |
| 5,186,097 | * 2/1993 | Vaseloff et al. | 99/330 |
| 5,433,105 | 7/1995 | Takahashi et al. . | |
| 5,545,877 | 8/1996 | Shelton . | |
| 5,582,755 | 12/1996 | Maher, Jr. et al. . | |
| 5,591,901 | 1/1997 | Heckman . | |
| 5,598,767 | * 2/1997 | Minari et al. | 99/332 |
| 5,942,269 | 8/1999 | Casey et al. . | |
| 6,034,359 | * 3/2000 | Busch | 219/497 |

FOREIGN PATENT DOCUMENTS

| | | |
|---|---|---|
| 2648865 | * 5/1978 | (DE) . |
| 3621999 | * 1/1987 | (DE) . |
| 3938823 | * 5/1991 | (DE) . |
| 62-166226 | * 7/1987 | (JP) . |
| 1-158915 | * 6/1989 | (JP) . |
| 1-247915 | * 10/1989 | (JP) . |
| 7-151722 | * 6/1995 | (JP) . |
| 961161 | * 9/1982 | (SU) . |

OTHER PUBLICATIONS

Palaniappan, S. et al., "Electrical Conductivity of Selected Juices: Influences of Temperature, Solids Content, Applied Voltage, and Particle Size", Journal of Food Process Engr., vol. 14, No. 4, 1991.*

* cited by examiner

Primary Examiner—John A. Jeffery
(74) Attorney, Agent, or Firm—Baker Botts L.L.P.

(57) ABSTRACT

The invention is directed to an apparatus for identifying a subject medium from several possible subject media within a cooking device, such as deep fat fryer. The apparatus contains one subject medium within the cooking device and has a controller, which includes a timer, and generates a conductivity signal. The apparatus also includes a conductivity measuring device which receives the conductivity signal and measures a conductivity value device in response to the conductivity signal. The controller determines the subject medium's composition by comparing the measured conductivity value to predetermined conductivity values for the known group of subject media.

19 Claims, 6 Drawing Sheets

APPARATUS AND METHOD FOR IDENTIFYING SUBJECT MEDIUM WITHIN COOKING DEVICE

BACKGROUND OF THE INVENTION

1. Field of the Invention

This invention relates to deep fat cooking devices generally, and more particularly, to apparatus and methods for identifying subject medium within such cooking devices.

2. Description of the Related Art

Large capacity, pressurized, deep fat fryer cookers are known in the art and have been devised for cooking food products in a heated or pressurized environment, or both. Such devices may include a cooking vessel, referred to as a fry pot, which may be filled with a subject medium, such as oil, shortening, water, or the like, and heating elements surrounding or immersed in the vessel, or both, for heating the subject medium. Food products may be placed in the cooking vessel, either directly or in a container, such as a wire basket, and are cooked for a desired length of time.

These cooking devices may have a temperature probe, a heating element, and a temperature selector for enabling a user to select a desired cooking temperature. Control means control the heating element in different modes of operation corresponding to the different stages of preparing food products. Moreover, cooking devices usually provide for proper maintenance of the subject medium. Specifically, if shortening is used, it is desirable to filter the shortening periodically to reduce or eliminate adverse effects on cooking quality due to the absorption by the shortening of oils and odor associated with the cooked food products, and degradation of the shortening, e.g., its breakdown due to heat, extended use, and other factors. Thus, the subject medium may be drained periodically in order to be filtered.

After repeated use, the cooking devices themselves also may need to be cleaned and maintained in order to insure quality in cooking operations. Fryer operators often use water-based cleaning solutions in the fry pots within the cooking devices. While generally an effective cleaning method, the use of water to clean the fry pot may cause uncertainty of the proper temperature level needed to operate the cooking device if the operator is not sure if water or cooking oil is placed therein. It is desirable to limit the water temperature to less than the boiling point to prevent boilers. Thus, it is desirable for operators and process controllers to be able to distinguish between water and cooking mediums in a fry pot.

SUMMARY OF THE INVENTION

In an embodiment, the invention is an apparatus for identifying at least one of a plurality of subject media within a cooking device. The apparatus comprises a cooking vessel for holding at least one subject medium within the cooking device, and a controller, including a timer, which generates a conductivity measurement signal. The apparatus further comprises a conductivity measuring device. The conductivity measuring device receives the conductivity signal and, in response to the conductivity signal, measures a conductivity value of the subject medium surrounding the conductivity measuring device. The controller determines the subject medium's composition by comparing the measured conductivity value to a plurality of predetermined conductivity values for the plurality of subject media.

In another embodiment, the invention is a method for identifying at least one of a plurality of subject media within a cooking device. The method comprises the steps of providing a cooking vessel containing at least one subject medium device and generating a conductivity signal. The method further comprises the step of measuring a conductivity value of the subject medium in response to the conductivity signal. The method comprises the step of comparing the measured conductivity value to a plurality of predetermined conductivity values for the plurality of subject media and matching the measured conductivity value with at least one of the plurality of predetermined conductivity values to identify the subject medium.

An object of the present invention is to provide an apparatus that identifies a subject medium using the medium's conductivity. It is a feature of this invention that it includes a controller adapted to measure conductivity to identify the subject medium. It is an advantage of this invention that time and costs are reduced or minimized by accurately identifying whether the subject medium is water or oil.

It is another feature of this invention that it is adapted to perform do these determinations automatically, without operator intervention. It is an advantage of this invention that time and costs are reduced or minimized by not requiring operator intervention.

It is another object of this invention that the identification of a subject medium may be performed by a single apparatus on a plurality of devices. It is a feature of this invention that a controller is adapted to be programmed with data corresponding to a particular system. It is an advantage of this invention that it reduces or minimizes costs by being adaptable to a plurality of systems.

Other objects, features, and advantages will be understood in view of the following description of preferred embodiments with respect to the drawings.

BRIEF DESCRIPTION OF THE DRAWINGS

For a more complete understanding of the present invention and the objects, features, and advantages thereof, reference is now made to the following descriptions taken in connection with the accompanying drawings in which:

FIG. 3b-1 illustrates a graphical representation of a voltage pulse detected by the sensing circuit depicted in FIG. 3a in accordance with the present invention.

FIG. 3b-2 illustrates a graphical representation of a voltage pulse detected by the sensing circuit depicted in FIG. 3a in accordance with the present invention.

DETAILED DESCRIPTION OF PREFERRED EMBODIMENTS

Preferred embodiments of the present invention and their advantages may be better understood by referring to FIGS.

1 through 5 of the drawings. The same numerals are used for corresponding parts of the various drawings.

Figure 1:
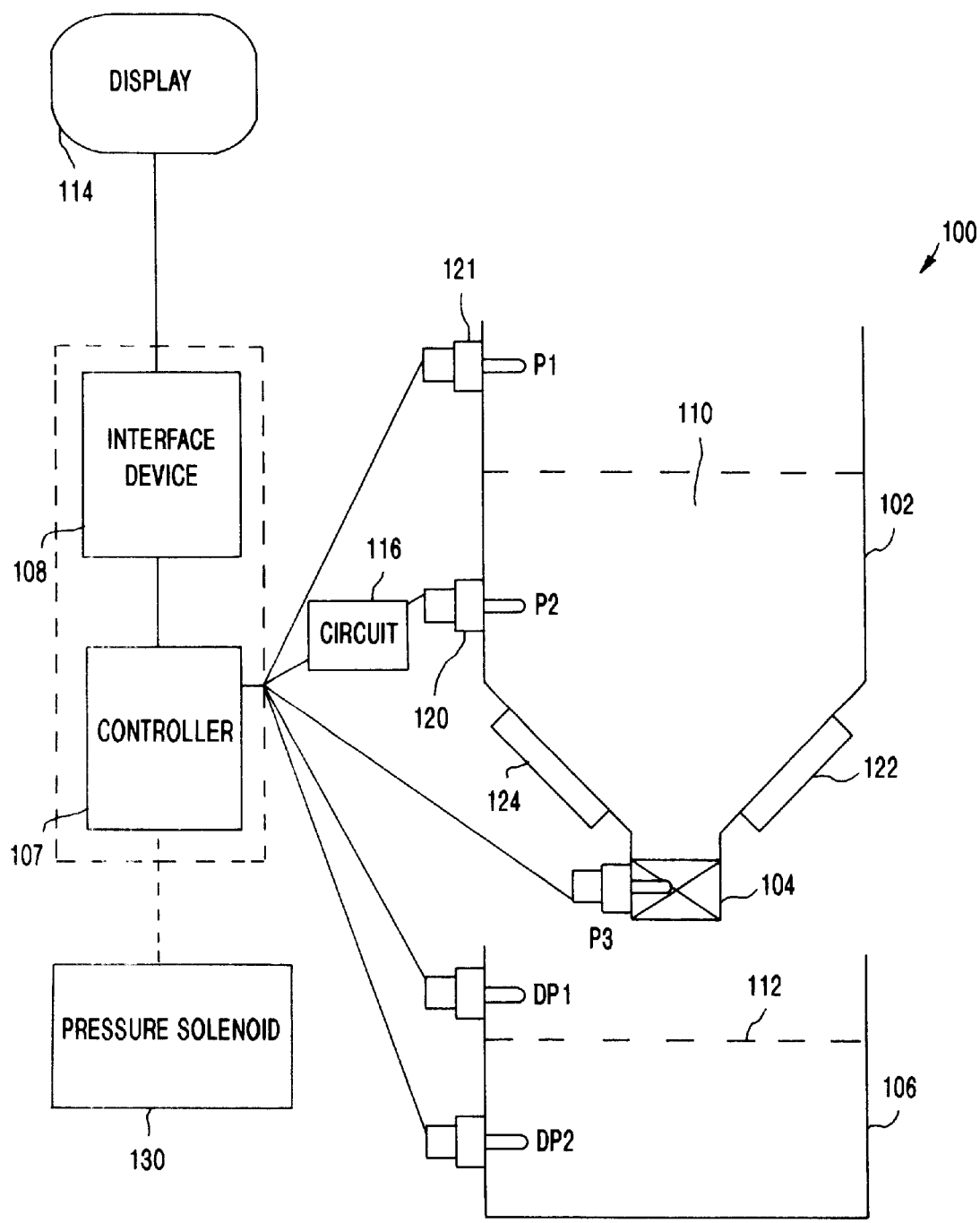
FIG. 1 depicts a schematic of an apparatus for identifying a subject medium within a cooking device in accordance with the present invention.

Referring to FIG. 1, a cooking device 100 is depicted. In a preferred embodiment, cooking device 100 may be a deep fat fryer. Cooking device 100 comprises a fry pot 102, including a drain valve 104. Fry pot 102 acts as a cooking vessel for cooking device 100. A subject medium 110 is placed in fry pot 102 for cooking operations. Subject medium 110 may be a cleaning medium, such as water, or a cooking oil, such as shortening, lard, peanut oil, or vegetable oil. Subject medium 110 is drained from the cooking device 102 by drain valve 104.

A controller 107 transmits commands to different components within cooking device 100. These commands may include a command to commence heating fry pot 102, to perform measurements on subject medium 110, or to relay information to an interface device 108. Interface device 108 may be linked to a display 114.

Further, display 114 is adapted for displaying the identity of subject medium 110 and other related information to an operator. Display 114 may be a plurality of light emitting diodes (LEDs), a cathode-ray tube (CRT), a liquid crystal display (LCD), a 7 or 13 segment display, or the like that presents information to an operator. Controller 107 also may include a timer (not shown) that is adapted to measure time either continuously or at discrete intervals.

A sensor 120, attached to the inside wall of fry pot 102, is in contact with subject medium 110. Sensor 120 is connected to controller 107 and receives commands transmitted by controller 107. Sensor 121 also is attached to the inside wall of fry pot 102. In an embodiment, sensor 121 is not in contact with subject medium 110. Signals generated by sensor 120 are relayed to controller 107. In an embodiment, the signals may be relayed via sensing circuit 116. Sensing circuit 116 is connected to a power supply (not shown). Sensing circuit 116 is discussed in further detail with reference to FIG. 3a. These signals then are communicated to an operator on display 114 via interface device 108 with controller 107. An operator also may use the interface device 108 to transmit commands to controller 107 to perform cooking, cleaning, and other operations.

Heaters 122 and 124 may be secured to fry pot 102. When activated, heaters 122 and 124 raise the temperature of subject medium 110. Signals from controller 107 activate and deactivate heaters 122 and 124. In another embodiment, subject medium 110 is pressurized by engaging a pressure solenoid 130. Pressure solenoid 130 receives commands from controller 107 and when engaged, pressurizes fry pot 102 above atmospheric pressure.

Cooking device 100 includes a drain pan 106 for receiving subject medium 110 from fry pot 102. Drain valve 104 transfers the cooking substance from fry pot 102 to drain pan 106. For example, fry pot 102 may be drained periodically in order to filter subject medium 110, or to clean the various cooking components of fry pot 102.

Figure 2:
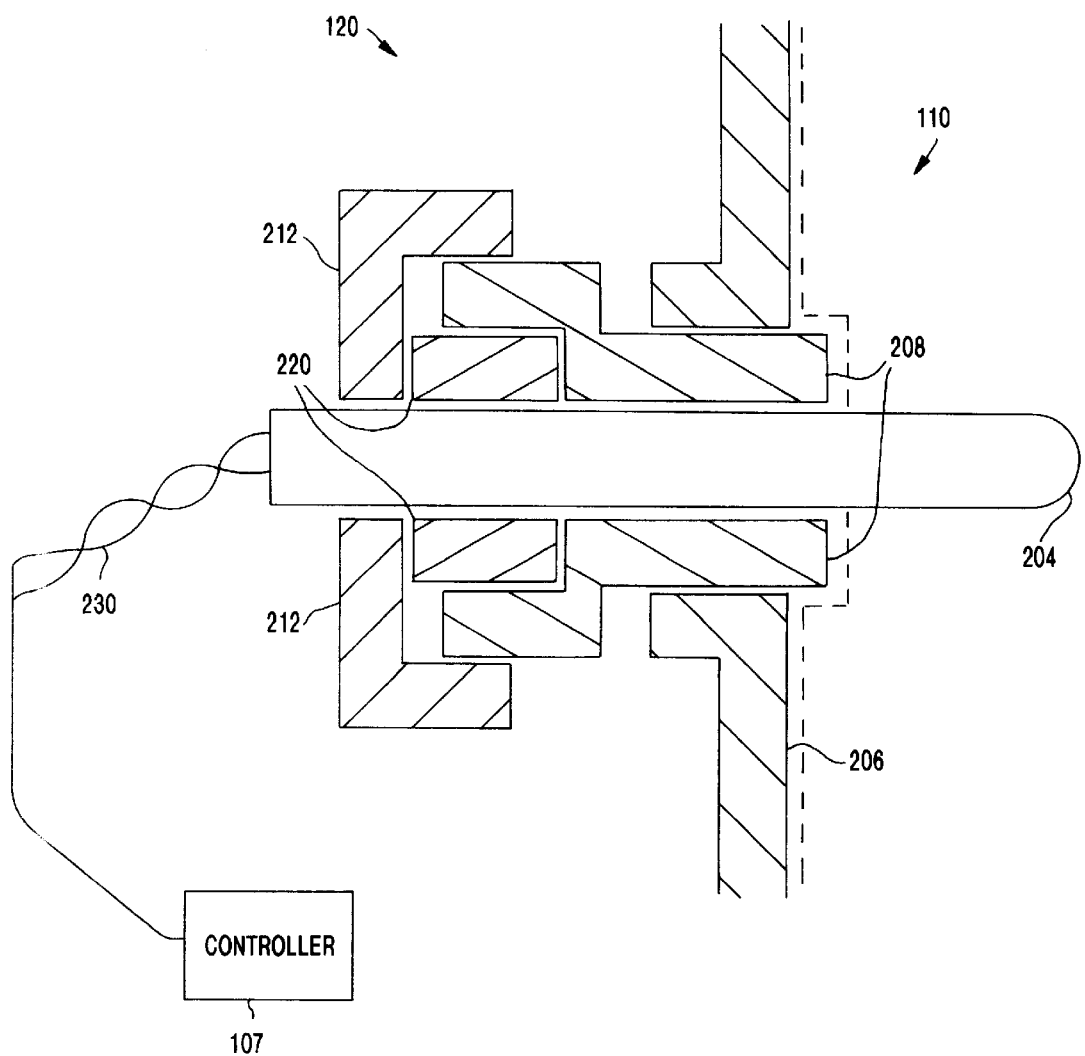
FIG. 2 depicts a sensor for measuring conductivity of a subject medium within a cooking device in accordance with the present invention.

Referring to FIG. 2, an embodiment of sensor 120 is depicted. Sensor 120 generates signals corresponding to temperature and resistance measurements, which then are relayed to controller 107. Sensor 120 includes a probe 204 fitted within fry pot wall 206 and connects to controller 107 by wires 230. Probe 204 is secured by fitting 208. Further, probe 204 is electrically insulated by insulator 220. Probe 204 is secured by nut 212. Probe 204 also may be used as a temperature measuring device to relay temperature measurements to controller 107. Referring to FIG. 2, a cross-sectional view of fitting 208, insulator 220, and nut 212 is depicted.

In temperature determinations, probe 204 measures the temperature of subject medium 110. This measurement is relayed to controller 107. Probe 204 also may be used to make resistance measurements when commanded by controller 107. Probe 204 is mounted by fitting 208. Fitting 208 may be fabricated from stainless steel. Probe 204 is electrically insulated from fry pot wall 206 by insulator 220, which is sealed with Teflon® tape. Stainless steel fitting 208 protrudes through fry pot wall 206 into subject medium 110. The resistance between fry pot wall 206 and stainless steel fitting 208 is measured. The resistance measurement then determines the conductivity of subject medium 110.

Figure 3A:
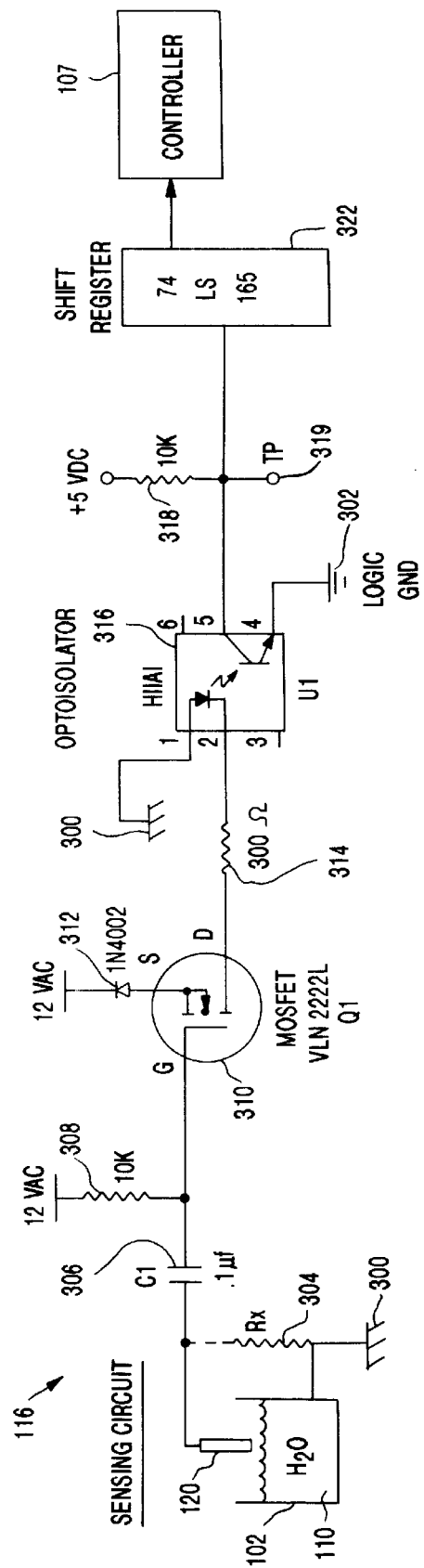
FIG. 3a depicts a sensing circuit for measuring conductivity of a subject medium within a cooking device in accordance with the present invention.

With reference to FIG. 3a, a sensor circuit 116 is depicted. Sensor circuit 116 connects to probe 120. Probe 120 is immersed within cooking medium 110 in fry pot 102. The wall of fry pot 102 completes sensor circuit 116 when cooking medium 110 is present. Resistor 304, or Rx, represents the resistance between probe 120 and the wall of fry pot 102. In an embodiment, resistor 304 is the resistance of cooking medium 110 between probe 120 and the wall of fry pot 102. If cooking medium 110 is water, resistor 304 may be less than 50 Kohms. The resistance measurement is performed with an alternating current ("AC") excitation voltage to avoid known galvanic corrosion effects associated with conductivity measurements in fluids. A voltage of 12 volts AC acts as the excitation voltages at twice prevailing main frequencies, either 100 or 120 Hz. Resistor 304 also connects to ground 300.

Capacitor 306 is coupled to probe 120 and resistor 304. Capacitor 306 blocks Direct Current ("DC") voltage to probe 120. Preferably, capacitor 306 is 0.1 uf. Resistor 308 forms a voltage divider with resistor 304. Preferably, resistor 308 is 10 Kohms. Resistor 308 is one leg of voltage divider formed by resistor 308, capacitor 306 and resistor 304. If 12 volts AC is applied, the voltage generated by resistors 304 and 308 is expressed by ((Rx)/(Rx+10 Kohms))×10 volts, or 2 volts when Rx=50 Kohms (water). Resistor 308 connects to capacitor 306 and switching MOSFET 310.

Switching MOSFET 310 serves to buffer the resistor 308/resistor 304 voltage divider for subsequent processing, and to drive the output optoisolator 316. Diode 312 supplies switching MOSFET 310 with half-wave rectified AC, and biases switching MOSFET 310's source pin one diode drop or about 0.8 volts, above the gate voltage to ensure complete turn-off of switching MOSFET 310. Preferably, switching MOSFET 310 turns on when the gate voltage is between about 0.6 volts and about 2.5 volts. More preferably, switching MOSFET 310 turns on when the gate voltage is about 1.8 volts.

Optoisolator 316 performs two functions. First, optoisolator 316 performs level shifting to convert the AC signal to a single-supply TTL—compatible signal. Second, optoisolator 316 provides some measure of electromagnetic interference immunity. Resistor 314 limits optoisolator 316 LED drive current. Preferably, resistor 314 is 300 ohms. Resistor 318 supplies collector current for optoisolator 316 output transistor. Resistor 318 receives 5 volts DC to supply the collector current. Optoisolator 316 connects to logic ground 302. Shift register 322 multiplexes the optoisolator 316 output with other process input signals that are read by controller 107.

Sensing circuit 116 results in a TTL-capatible compatible output signal with a duty cycle which varies as a function of the resistance 304 of cooking medium 110 and fry pot 102. The following table depicts results from measuring the resistance of a cooking medium in an output "off" time.

| Rx | Output "off" time |
| --- | --- |
| 0 ohms | 5.4 mS |
| 10 Kohm | 5.7 mS |
| 20 Kohm | 5.8 mS |
| 30 Kohm | 5.8 mS |
| 40 Kohm | 5.5 mS |
| 50 Kohm | 5.0 mS |
| 60 Kohm | 4.6 mS |
| 70 Kohm | 3.6 mS |
| 80 Kohm | 1.5 mS |
| 90 Kohm | 0 |
| 100 Kohm | 0 |

By measuring the "low" time of the output signal from optoisolator 316, controller 107 infers that fry pot 102 contains water as cooking medium 110 and is indicated by relatively long off-time, or fry pot 102 contains shortening or is empty, indicated by relatively short off-time. Because of the resistance of shortening is substantially greater than 100 Kohm, and the resistance of water is on the order of hundreds of ohms, such as 50 Kohm. The resistance value corresponds to an off-time of 5.0 mS.

Figures 1, 3B:
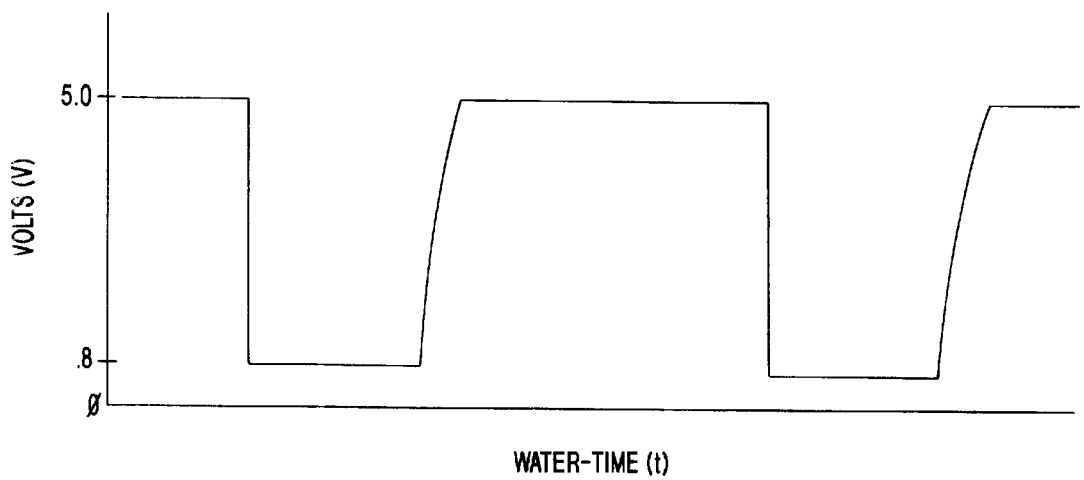
Figures 2, 3B:
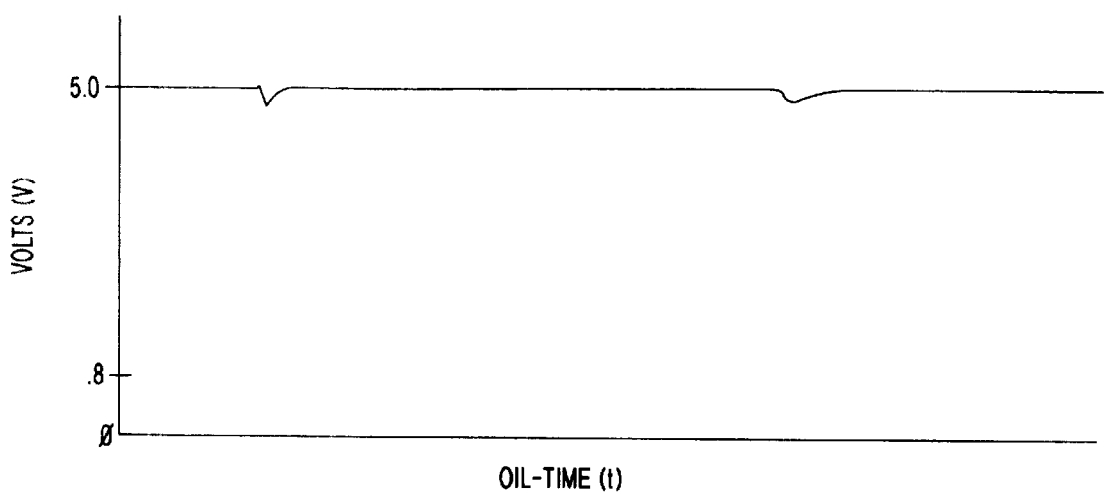

Preferring to FIG. 3b-1, a graphical representation of a voltage pulse detected by sensing circuit 116. FIG. 3b-1 depicts the output signal from sensing circuit 116 as voltage is applied to water as cooking medium 110 within fry pot 102. As noted by line A, 5 volts, or logic "1", outputs as voltage is applied and represents a logic "one." The output of optoisolator 316 drops the applied voltage at test point 319 to a logic "0" voltage on a periodic basis. As test point 319 drops voltage level to logic "0," the output signal shows a voltage of 0.8 volts, or line B, in FIG. 3b-1. Water provides little resistance such that the voltages level is able to drop in a timely manner to low, as indicated in the table above, and may be held for a period.

Referring to FIG. 3b-2, a graphical representation of another voltage pulse detected by sensing circuit 116 is depicted. Sensing circuit 116 outputs 5 volts DC, or logic "1," as voltage is applied to il as cooking medium 110 within fry pot 102. Test point 319 toggles sensing circuit 116 to reduce the output voltage to 0.8 volts, or logic "0." Because of the poor conductivity of oil, the logic 0 state is not timely reached when applied by test point 319. Line A depicts the output voltage. The output voltage does not reach logic 0. Thus, the large resistance of oil as cooking medium 110 prevents a logic 0 state from being achieved, as indicated in the table above.

As depicted in FIGS. 3b-1 and 3b-2, the resistance differences between water and oil are of a magnitude that a conductivity measurement may be used in distinguishing the mediums.

Figure 4:
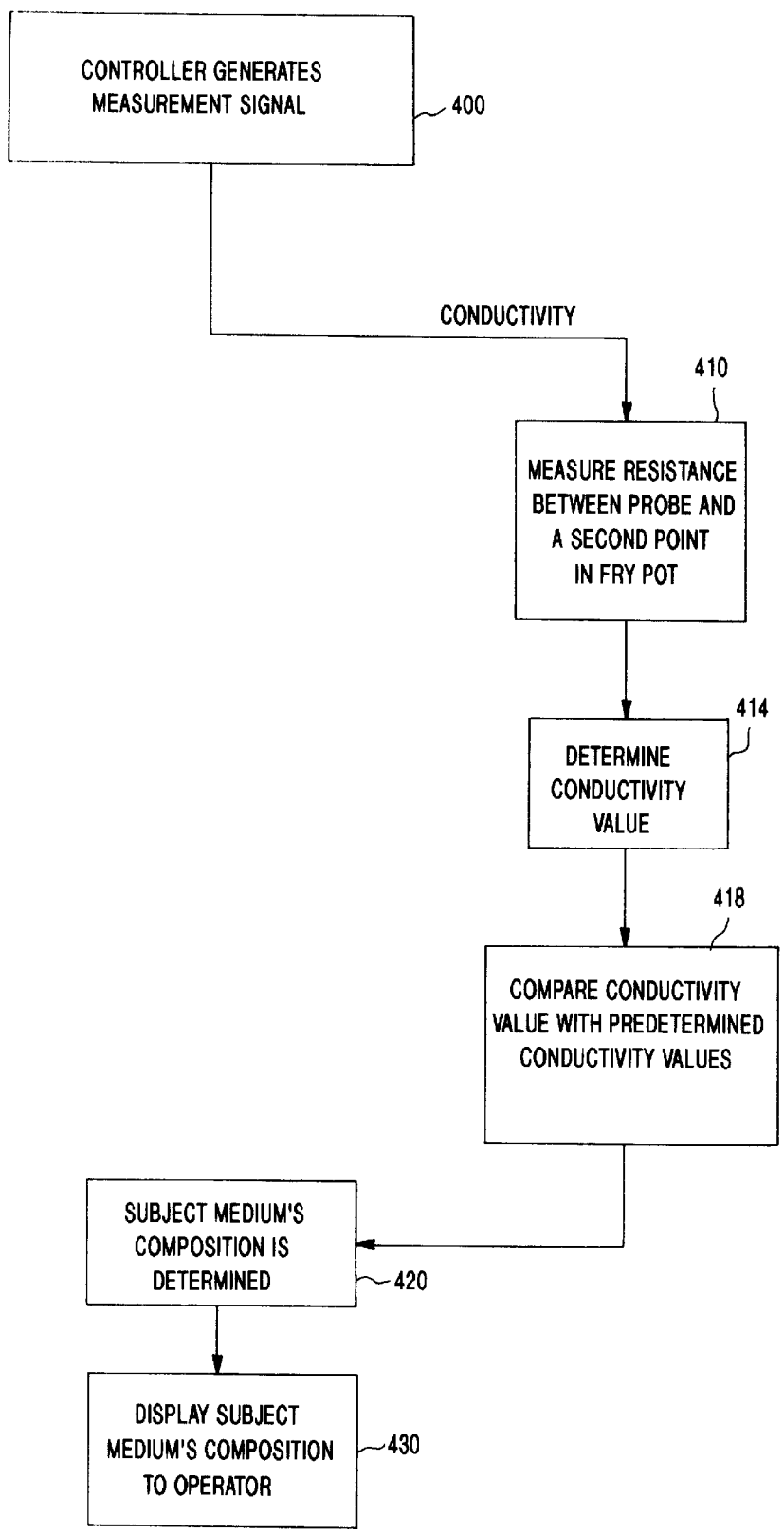
FIG. 4 illustrates a flow chart of a method for identifying a subject medium within a cooking device in accordance with the present invention.

In another embodiment, a method for identifying a subject medium within a cooking device is provided. Referring to FIG. 4, in step 400, controller 107 generates a measurement signal selected automatically or by an operator. Cooking device 100 may also command controller 107 to generate a signal. The system may also query an operator whether the identification method may be performed prior to applying any heat to fry pot 102. The measurement signal includes a conductivity signal.

In step 410, a conductivity value is measured by determining the resistance between a probe and a second point on fry pot 102. For example, the resistance measurement may be taken between stainless steel fitting 208 and probe 204 as depicted in FIG. 2. This resistance measurement is used to determine a conductivity value of subject medium 110 in step 414. For example, the bulk resistance of oil is at least several meg ohms, even when contaminated with common cooking by-products, such as salt. In contrast, the bulk resistance of water is significantly less than a hundred ohms and frequently only a few ohms if contaminated with cooking by-products. Thus, in step 418, this large difference is used in a comparison of the measured conductivity value of the subject with conductivity values of water and cooking oils. A large conductivity value, i.e., low resistance, of the subject medium, indicates that water is in fry pot 102. A small conductivity value, i.e., large resistance, indicates that a cooking medium, such as shortening or another cooking oil, is in fry pot 102. Controller 107 may be programmed to include these values, and these programmed values determine the composition of subject medium 110 in cooking device 100.

In step 420, controller 107 uses the predetermined values of the conductivity of a known media and matches the predetermined values with the measured values to determine the composition of subject medium 110. This match identifies whether subject medium 110 is water or a cooking oil. After the determination is made, in step 430, this information about the composition of subject medium 110 may be displayed to an operator. For example, if the operator is uncertain whether the cooking device 100 holds water or shortening, a conductivity measurement is executed to determine the composition of subject medium 110 and to inform the operator before cooking operations commence. In another embodiment, such a determination may be made by cooking device 100 prior to applying any heat to subject medium 110. Because the boiling point of oil is higher than water, an initial determination may be desired to prevent super-heating of the water. Thus, cooking device 100 prevents activation of heaters 122 and 124 if cooking medium 110 is water. Alternatively, pressure 130 does not engage if cooking medium 110 is water.

Figure 5:
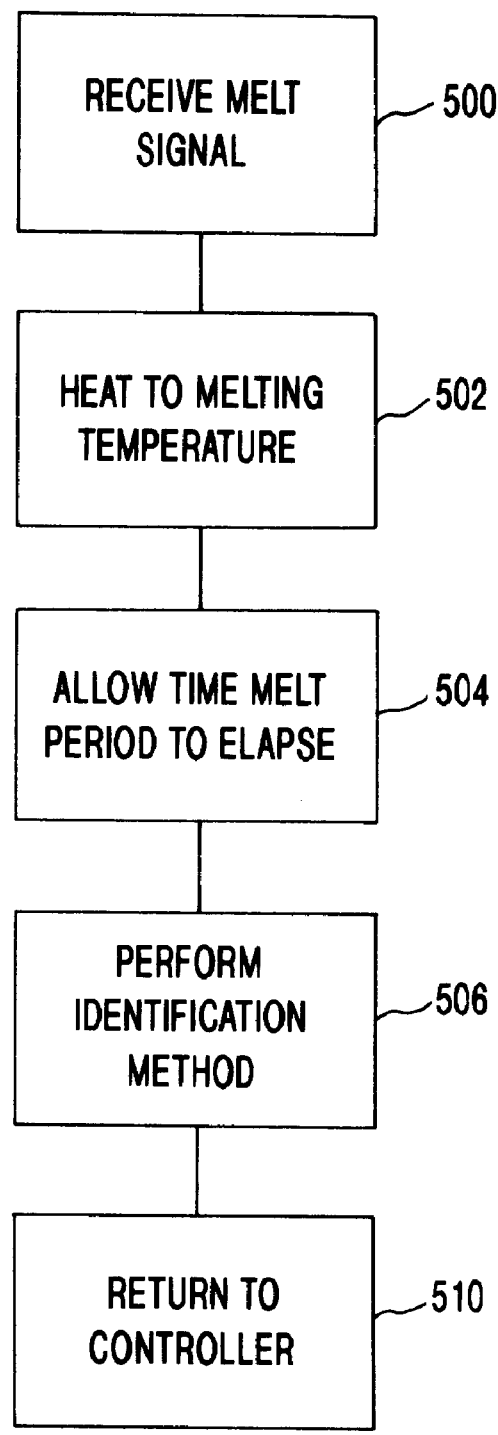
FIG. 5 illustrates a flow chart of a method for melting a subject medium within a cooking device in accordance with the present invention.

In another embodiment, a method for insuring that subject medium 110 is melted prior to attempting identification is disclosed. The subject medium may not be properly identified if it is not in a liquid state. Referring to FIG. 5, a melt signal is generated by the controller 107 and received in step 500. Again, controller 107 may generate the melt signal in response to an operator request or system requirements. Upon receipt of the melt signal, cooking device 100 enters a melt mode. No temperature or resistance measurements may be taken while the melt mode is in progress. In step 502, heaters 122 and 124 are activated to increase the temperature of subject medium 110 to a melting temperature range. This melting temperature range may be equal to the melting temperature of shortening used in cooking operations. Preferably, this temperature is in the range of about 71° C. to about 82° C. It may also be desirable to keep the melting temperature range below the boiling point of water, i.e., less than about 100° C. This limit on the melting temperature range prevents temperatures from exceeding the boiling point of water, yet melts shortening and other cooking mediums in cooking device 100.

In step 504, a time melt period is allowed to elapse, so that the transition from solid to liquid shortening is made. This time melt period may be retrieved from controller 107 or input by the operator. During this time melt period, cooking device 100 may use a variety of methods to melt the liquid shortening, such as pulse heating. After the time period has elapsed, the system may perform, step 506 executes the method disclosed in FIG. 4 to identify whether subject medium 110 is water or a cooking medium. The melting mode has been completed and other operations may be performed in cooking device 100. By performing the melting mode, the system ensures that faulty or erroneous measurements are not taken and subject medium 110 is not misidentified. In step 510, command is returned to controller 107.

While preferred embodiments of the invention have been described in detail with respect to the drawings, it will be understood by those skilled in the arts that modifications in form and detail may be made without departing from the spirit and scope of the invention. Other embodiments will be apparent to those skilled in the art from a consideration of the specification or practice of the invention disclosed herein. It is intended that the specification and examples be considered as exemplary only, with the true scope and spirit of the invention being indicated by the following claims.

I claim:

1. A medium identification apparatus for identifying at least one of a plurality of subject media within a cooking device, comprising:

a cooking vessel for holding at least one subject medium within said cooking device;

a controller, including a timer, generating a conductivity signal;

a conductivity measuring device, which receives said conductivity signal and measures a conductivity value of said at least one subject medium surrounding said conductivity measuring device in response to said conductivity signal; and said controller determines a composition of said at least one subject medium by comparing said measured conductivity value to a plurality of predetermined conductivity values for said plurality of subject media when said conductivity signal is selected.

2. The apparatus of claim 1, wherein said cooking device includes a heater.

3. The apparatus of claim 1, further comprising an interface device generates a display of said composition of said at least one subject medium.

4. The apparatus of claim 1, further comprising a melt mode, wherein said controller generates a melt signal that activates said heater for a time melt period, such that the temperature of said at least one subject medium is within a melting temperature range after completion of said melt mode.

5. The apparatus of claim 1, wherein said cooking vessel is a fry pot.

6. The apparatus of claim 1, wherein said conductivity measuring device are enclosed in a sensor in said cooking device.

7. The apparatus of claim 1, wherein said cooking device is a pressure flyer.

8. The apparatus of claim 7, wherein said pressure fryer has a pressure solenoid, said pressure solenoid deactivates when commanded by said controller.

9. An apparatus for identifying at least one of a plurality of subject media within a cooking device, comprising:

at least one subject medium within said cooking device;

a controller, including a timer, said controller generating a conductivity signal;

a conductivity measuring device for receiving said conductivity signal and for measuring a conductivity value of said at least one subject medium surrounding said conductivity measuring device in response to said conductivity signal;

a conductivity comparative device, wherein said measured conductivity value is matched to a plurality of predetermined conductivity values for a corresponding plurality of subject media to said conductivity signal; and said controller determining said subject medium's composition with said matched conductivity value.

10. A method for identifying at least one of a plurality of subject media within a cooking device, comprising the steps of:

providing a cooking vessel containing at least one subject medium;

generating a conductivity signal;

measuring a conductivity value of said at least one subject medium in response to said conductivity signal;

comparing said measured conductivity value to a plurality of predetermined conductivity values for said plurality of subject media when said conductivity signal is generated; and matching said measured conductivity value with at least one of said plurality of predetermined conductivity values to identify said at least one subject medium when said conductivity signal is generated.

11. The method of claim 10, further comprising the step of:

generating a display indicating said composition of said subject medium on an interface device.

12. The method of claim 10, further comprising the step of:

generating a melt signal, wherein said melt signal activates said heater for a time melt period, such that the temperature of said at least one subject medium is within a melting temperature range in response to said melt signal.

13. A medium identification apparatus for identifying at least one of a plurality of subject media within a cooking device, comprising:

a cooking vessel for holding at least one subject medium within said cooking device;

a controller, including a timer, generating a conductivity signal;

a conductivity measuring device, which receives said conductivity signal and measures a conductivity value of said at least one subject medium surrounding said conductivity measuring device in response to said conductivity signal, a melt mode, wherein said controller generates a melt signal that activates said heater for a time melt period, such that the temperature of said at least one subject medium is within a melting temperature range after completion of said melt mode; and said controller determines a composition of said at least one subject medium by comparing said measured conductivity value to a plurality of predetermined conductivity values for said plurality of subject media when said conductivity signal is selected.

14. The apparatus of claim 13, wherein said cooking device includes a heater.

15. The apparatus of claim 13, further comprising an interface device generates a display of said composition of said at least one subject medium.

16. The apparatus of claim 13, wherein said cooking vessel is a fry pot.

17. The apparatus of claim 13, wherein said conductivity measuring device is enclosed in a sensor in said cooking device.

18. The apparatus of claim 13, wherein said cooking device is a pressure fryer.

19. The apparatus of claim 18, wherein said pressure fryer has a pressure solenoid, said pressure solenoid deactivates when commanded by said controller.

* * * * *

UNITED STATES PATENT AND TRADEMARK OFFICE
CERTIFICATE OF CORRECTION

PATENT NO. : 6,274,850 B1
DATED : August 14, 2001
INVENTOR(S) : Gary L. Mercer

It is certified that error appears in the above-identified patent and that said Letters Patent is hereby corrected as shown below:

<u>Title page,</u>
Item [56], U.S. PATENT DOCUMENTS,
delete "5,086,324" and insert -- 5,088,324 --

Signed and Sealed this

Ninth Day of April, 2002

Attest:

JAMES E. ROGAN
Attesting Officer     Director of the United States Patent and Trademark Office